United States Patent [19]

Battista

[11] 4,416,814

[45] * Nov. 22, 1983

[54] PROTEIN POLYMER HYDROGELS

[76] Inventor: Orlando A. Battista, 3725 Fox Hollow Rd., Fort Worth, Tex. 76109

[*] Notice: The portion of the term of this patent subsequent to Apr. 28, 1998 has been disclaimed.

[21] Appl. No.: 416,475

[22] Filed: Sep. 10, 1982

Related U.S. Application Data

[63] Continuation-in-part of Ser. No. 246,660, Mar. 23, 1981, Pat. No. 4,349,470, which is a continuation-in-part of Ser. No. 74,014, Sep. 14, 1979, Pat. No. 4,264,493, which is a continuation-in-part of Ser. No. 952,303, Oct. 18, 1978, abandoned.

[51] Int. Cl.$^3$ .................... C07G 7/00; C08H 1/00; C08H 1/06; C08H 9/00
[52] U.S. Cl. ............................ 260/117; 3/1.9; 106/125; 106/135; 106/154 R; 106/161; 128/92 C; 260/112 R; 260/123.5; 260/123.7; 264/1.1; 351/160 H; 351/160 R; 351/161; 351/162; 424/177; 424/359; 424/360
[58] Field of Search ............ 260/112 R, 123.5, 123.7, 260/117; 106/161, 125; 264/1.1

[56] References Cited

U.S. PATENT DOCUMENTS

| | | | |
|---|---|---|---|
| 3,099,562 | 7/1963 | Rogers | 260/112 R X |
| 3,157,524 | 11/1964 | Artandi | 106/122 |
| 3,393,080 | 7/1968 | Erdi et al. | 260/123.7 X |
| 3,443,261 | 5/1969 | Battista et al. | 260/123.7 UX |
| 3,607,860 | 9/1971 | Yamato et al. | 260/123.5 |
| 3,628,974 | 12/1971 | Battista | 260/123.7 X |
| 3,649,347 | 3/1972 | Battista | 260/123.7 X |
| 3,691,281 | 9/1972 | Battista | 260/123.7 |
| 3,767,437 | 10/1973 | Cruz | 106/161 |
| 3,823,212 | 7/1974 | Chvapil | 260/123.7 X |
| 3,965,063 | 6/1976 | Holcombe | 264/1 X |
| 4,096,870 | 6/1978 | Manfuso | 264/1 X |
| 4,121,885 | 10/1978 | Erickson et al. | 264/1 X |
| 4,123,408 | 10/1978 | Gordon | 264/1 X |
| 4,264,493 | 4/1981 | Battista | 260/123.7 X |
| 4,349,470 | 9/1982 | Battista | 260/123.7 X |

*Primary Examiner*—Howard E. Schain
*Attorney, Agent, or Firm*—George F. Mueller

[57] ABSTRACT

Protein hydrogel structures formed from natural proteins having an average molecular weight of about 100,000 or less by dissolving the protein in an aqueous acidic solution, subjecting the protein to vapor phase crosslinking with at least two crosslinking agents, and air drying to a moisture content not exceeding 10 percent. The drying may be effected by treatment with a water-miscible organic solvent or by air drying. The structures may be in the form of soft contact lenses, films, fibers, and prosthetics.

20 Claims, No Drawings

PROTEIN POLYMER HYDROGELS

This application is a continuation-in-part of application Ser. No. 246,660 filed Mar. 23, 1981, now U.S. Pat. No. 4,349,470, which is a continuation-in-part of application Ser. No. 74,014 filed Sept. 14, 1979, now U.S. Pat. No. 4,264,493, which is a continuation-in-part of application Ser. No. 952,303 filed Oct. 18, 1978, now abandoned.

This invention relates to hydrogel forms of natural animal and vegetable proteins which have properties superior to the properties of products prepared in accordance with the method disclosed in the parent application. It more specifically relates to improved compositions and products such as soft contact lenses (disposable, fugitive, and dressing forms), and cosmetic, pharmaceutical, and surgical preparations containing these forms of natural animal and vegetable proteins when used in contact with aqueous liquids. The invention also relates to methods of producing the improved products from such natural proteins.

By natural hydrogel (hydrocolloidal) animal or vegetable protein polymers is meant throughout the specification and claims crosslinked protein polymers of natural origin having an average molecular weight of about 100,000 or less, capable of being swollen by water over a wide range of water contents ranging from as low as 30 percent to 1000 percent and higher based on dry weight while possessing useful rheological control properties for specific end product uses.

This invention provides soft contact lenses capable of being colored completely or at least partly, if desired, using effective protein dyes, lenses that will correct optical defects of the wearer's eye.

This invention also provides contact lenses that may be worn continuously until they become cloudy—and can be thrown away (disposable) and replaced by a fresh lens or a pair of lenses.

The invention also provides a means of controlling the properties of contact lenses—using the same raw materials—so that such lenses may have their properties so engineered in advance that they may be used as corneal dressings, fugitive lenses, or in the form of rigid rheologically-tailored hydrogels, capable of serving as a replacement for vitreous fluids.

This invention further provides a means for controlling the composition and chemistry of the natural protein hydrogels to produce burn and wound dressings having superior properties in the wet state.

A further object of the invention is to adapt this new technology to produce novel fibers for textile and medical uses.

The invention also provides a hydrogel base from which bone-like structures, arteries, and similar prostheses possessing outstanding properties in an aqueous fluid saturated state never before available.

The art has long worked with low molecular weight proteins (such as animal gelatins) and vegetable proteins (such as soybean proteins)—using them with and without varying degrees and types of crosslinking. However, great limitations, especially in wet physical properties, of such prior products limited their use, especially in the structural forms described herein. For example, prior art has clearly concluded that gelatin or agar never were found suitable to produce contact lenses (Soft Contact Lens, by Montague Ruben, John Wiley & Song, p. 25, 1978).

The present invention provides improved forms of protein polymer structures that possess improved flexibility, tensile strength, elongation, optical acuity, and dimensional stability, particularly in the wet state and in contact with saline at body temperature (38° C.) as contrasted to the products of the prior applications. The improvements are critically dependent upon the specific sequence of manipulative processing. It is essential that the pH of the protein solution be maintained within certain limits during a vapor crosslinking reaction. Two or more crosslinking agents are utilized and they may be covalent and/or non-covalent in any combination. The protein solution may contain a crosslinking agent prior to the vapor phase reaction. Optionally, following the vapor phase treatment, the material may be subjected to an additional treatment by immersion in an organic solvent-water solution containing one or more crosslinking agents as described above. Further improvements are effected by subjecting the protein in the presence of the vapors of the crosslinking agents or in the solution of the crosslinking agents to UV and/or gamma radiation. Following the crosslinking treatment, the reaction is arrested by washing with water and the protein washed free of crosslinking agents. The protein is then dried so as to include not more than 10 percent moisture, preferably not more than 7 percent. Drying may be effected by solvent dehydration, air dried at temperatures not exceeding about 35° C., or drying under a vacuum. The products may be stored in dry state or, if used as, for example, a soft contact lens, the products may be stored in sterile saline.

In producing my products, it is essential to begin with natural protein raw materials that form clear solutions in water at concentrations up to 30 percent or higher. Ordinary household unflavored gelatin is a typical starting natural animal protein as one starting raw material for this invention and edible soybean protein is a typical starting vegetable protein example.

The products of the present invention are prepared from solutions of the natural protein containing from about 0.5 percent to about 30 percent, by weight, of the protein or mixtures of the proteins. The solution is heated to 60°±5° C. so as to aid in dissolving the protein and produce a clear solution. Following the dissolution of the protein, the pH of the solution is adjusted to about pH 3.5 from about pH 5.5 as by the addition of a suitable acid, such as, for example, hydrochloric or phosphoric acids, to form an aqueous acidic solution of the protein. While maintaining the acidic solution within the pH range, it is subjected to the vapors of the combination of crosslinking agents for at least 6 hours, preferably from 50 to 150 hours. A crosslinking agent may be incorporated in the protein solution prior to subjecting the solution to the vapor phase crosslinking reaction. Optionally, following vapor phase crosslinking, the treated solution may be immersed for from about 1 to 3 hours in an aqueous solution of an organic solvent containing one or more crosslinking agents. The improvements in physical properties may be further enhanced by subjecting the reaction mass (vapor phase and immersion in the solution) to UV and/or gamma radiation for a period of at least 2 hours.

The combination of crosslinking agents includes at least two crosslinking agents. Typical non-covalent crosslinking agents include ammonium alum, potassium alum, boric acid, and multivalent metal salts such as aluminum and calcium salts. Covalent crosslinking agents include aldehyde based compounds such as formaldehyde, glyoxal, glutaraldehyde, and the like. Other satisfactory covalent crosslinking agents are non-nitrogen polyfunctional compounds including, for example, epichlorhydrin, dichloropropanol, dichloromethyl and dichlorooctyl ethers, diepoxy-butane, ethylene glycol-dimethacrylate, diethylene glycol-dimethacrylate and the like. Further satisfactory covalent crosslinking agents are nitrogen containing polyfunctional compounds, including, for example, trichloroisocyanuric acid, hexamethylenediisocyante, ethylene-bis-methacrylamide, tetrachloropyrimidine, dimethylol urea, dimethylol ethylene urea, methylol and dimethylol acrylamide, and the like. A small amount of a peroxidic polymerization initiator, such as ammonium or potassium persulfate, and an activator, such as 2-dimethyleneaminomethyl-acetate or p-tolune sulfonic acid, may be included in the solution of the protein.

The solution of the protein is cast or shaped into a desired three-dimensional configuration or structure and subjected to the vapor phase crosslinking reaction for the desired period. The reaction is arrested by washing the structure with water and the structure washed free of crosslinking agents. The structure is then dried to a moisture content of not more than 10 percent, preferably not more than 7 percent, by air drying below 35° C. or by immersion in a mixture of water and a water-soluble organic solvent, such as, for example, ethanol, denatured alcohol, isopropanol, acetone, and the like. After the aqueous organic solvent solution treatment, the structure is washed free of the organic solvent with water and may be stored in saline. Alternatively, the structure may be air dried at temperatures not exceeding about 35° C. and stored in a dry state. The dry structures may be rehydrated readily by immersion in water or saline.

Because the base raw material is proteinaceous, products made in accordance with this invention lend themselves to being permanently dyed in single or multiple colored forms and designs, using dyeing procedures commonly applied to polymer materials containing —NH, —NH$_2$, and —COOH groups. Accordingly, any desired color either for functional or cosmetic purposes may be imparted to these products by the addition of suitable dyes or pigments.

The examples which follow are representative illustrations of the invention but are not to be considered as limitations.

EXAMPLE 1

SOFT CONTACT LENS

An ultrapure food grade gelatin having an average molecular weight of about 100,000 was dissolved in warm distilled water (60° C.) at a concentration of about 25 percent. The pH of the solution was adjusted to a pH of 4.5 to 5.0 with 10 N HCl. While maintained at a temperature of about 60° C., the solution was deaerated under a vacuum of about 30 inches. Using a micropipette, the deaerated gelatin solution was added to the convex counterparts of two-piece lens molds using an appropriate volume of 25 percent solution that would be required to produce a lens of fixed volume and a predetermined percent water of hydration. The concave counterparts of the two-piece lens molds were placed over the convex parts of the molds so as to produce an accurate closure between the two components of the two-piece molds. Clamps were used to hold the two parts of the molds tightly closed to insure a uniform edge around the enclosed lens templates within the two-part mold parts. The molds were placed in a refrigerator at a temperature of 4° to 5° C. overnight. The molds were separated with an intact gelatin template lens remaining on the convex part of the molds. At this cold temperature, it was possible to remove cleanly any flange overflow in the molds so that a clear lens template was exposed in precisely the dimension of the convex part of the mold, and the exact volume of the empty space formed when the two parts of the mold meet at the concave and convex edges, respectively. The convex counterparts of the molds carrying the lens templates were placed on a perforated plate and placed inside a bowl shaped plastic container. The plate had metal legs that supported it about an inch above the bottom of the plastic container. A 1.8 liter plastic bowl was used in this example.

The following mixture was prepared and blended thoroughly prior to being added carefully to the bottom of the plastic container to avoid any of the liquid touching the lenses on their respective molds:

1. 100 milliliters of a solution comprising 15 milliliters of Methyl Formcel (formaldehyde dissolved in methyl alcohol) and 85 milliliters of distilled water, plus
2. 5 milliliters of a 25 percent solution of biochemical grade of glutaraldehyde.

The lid of the container was immediately tightly sealed onto the top of the plastic container. The crosslinking reaction was allowed to go on in the vapor phase in the sealed container at room temperature (22° C.) for 120 hours. At the conclusion of the vapor crosslinking reaction, the crosslinked lenses on the convex components of the two-piece lens molds were dumped into warm tap water (about 80° C.) for about one minute to stop the crosslinking reaction and any free crosslinking agents were washed from the lenses. The lenses, still adhering to the convex components of the two-part lens molds, were soaked in a mixture of reagent grade ethyl alcohol (75 percent by volume) and distilled water (25 percent by volume) for 60 minutes to help sterilize the lenses and assist in the release of the lenses from their molds. Immersion of the lenses in this liquid for 60 minutes reduces their moisture content to about 10 percent. Some of the lenses were then washed with water and stored in sterile saline. The balance were washed in water and air dried to a moisture content of about 1 percent, stored dry, and rehydrated in sterile saline prior to use.

Lenses made in accordance with this example have superior physical properties—flexibility, tensile strength, extensibility, and dimensional stability as compared to the lenses made in accordance with examples of Serial No. 246,660, now Pat. No. 4,349,479. The lenses were crystal clear.

EXAMPLE 2

SOFT CONTACT LENS

The procedure of Example 1 was repeated through the 120 hour vapor phase crosslinking operation.

At the termination of the vapor phase treatment, the perforated plate carrying the convex counterparts of the molds with the lenses was immersed in a homogeneous solution containing 72.5 percent by volume reagent grade ethanol
25.0 percent by volume Methyl Formcel (formaldehyde dissolved in methanol)
2.5 percent by volume of a 25 percent solution of biochemical grade glutaraldehyde The solution was at room temperature (22° C.) and the period of immersion was 2 hours. The plate with the lenses on their molds was then placed in running cold tap water to arrest the crosslinking reaction and to wash the lenses free of crosslinking agents. The plate was then placed in a mixture of 75 percent by volume reagent grade ethanol and 25 percent by volume distilled water for about 60 minutes to sterilize the lenses and remove water from the lenses which assists in release of the lenses from the molds. The lenses were then washed with distilled water. Some of the lenses were then stored in saline. The balance of the lenses were dried in air at room temperature to a moisture content of about 10 percent and stored in such state.

The properties of the lenses were substantially identical to those of Example 1.

EXAMPLE 3

SOFT CONTACT LENS

Example 1 was repeated substituting a 20 percent gelatin solution at a pH of 4.5 to 5.0 and containing in 400 milliliters of total solution 500 drops of a 10 percent aqueous solution of edible grade ammonium alum.

EXAMPLE 4

SOFT CONTACT LENS

Example 2 was repeated substituting a 25 percent gelatin solution at a pH of 4.5 to 5.0 and containing in 400 milliliters of total solution 500 drops of a 10 percent aqueous solution of edible grade ammonium alum.

The products of Examples 3 and 4 had properties similar to the properties of the products of Example 1 although the tensile strength and dimensional stability in saline were somewhat enhanced.

In producing such products as contact lenses where crystal clarity is desired and yellow coloration must be maintained at a minimum, the proportion of glutaraldehyde during vapor phase crosslinking must not exceed about 5 percent by volume, preferably should be about 2.5 percent. For other products such as sausage casings, wound dressings, capsules, and the like 5 percent or more may be used where a coloration is not objectionable.

EXAMPLE 5

FILMS, BURN AND WOUND DRESSINGS

A 1000 milliliter clear gel mixture comprising a 20 percent gelatin solution (average molecular weight 80,000) was heated to 60° C. To this mixture was added with smooth, steady stirring 10 drops of 10 N HCl, bringing the pH to 4.50. Immediately thereafter, 10 milliliter of a 10 percent aqueous solution of ammonium alum, about 1 percent based on the gelatin, were added to the mixture with vigorous mixing, maintaining the temperature at 60°±5° C. Immediately after thoroughly mixing the above composition, it was deaerated in a vacuum desiccator 29 to 30 inches of vacuum. The mixture was next cast into flat Pyrex dishes the dimensions of which were chosen to reflect the final dimensions desired for the film. For example, a circular film or dressing may be made by using a Petri dish, a rectangular film by using a rectangular glass dish. As an alternative procedure, the gel may be spread using a "doctor blade" on a plastic surface. The hydrogel was allowed to partially dry slowly at room temperature (22° C.) for about 24 hours.

A mixture of a Methyl Formcel solution and glutaraldehyde solution as described in Example 1 was prepared and transferred to a plastic bowl. The partially dried films were removed from the Pyrex dishes and suspended in the bowl over the mixture of solutions. The bowl was sealed and a vapor phase crosslinking reaction allowed to proceed for about 100 hours at room temperature (22° C.). The films were then placed in running cold tap water to arrest the crosslinking reaction and to wash the films free of crosslinking agents. The films were then placed in ethanol-water mixture (75 percent ethanol, 25 percent distilled water, by volume) for 1 hour. The films were then washed with distilled water and air dried at room temperature (22° C.) to an 8 percent moisture content. The films were placed in sterile packages and stored. Before use as a wound dressing, the films may be hydrated readily by soaking in saline.

EXAMPLE 6

TUBES, CAPSULES, ARTERIES, AND OTHER STRUCTURAL FORMS

Using the same formulation described in Example 5, the deaerated hydrogel was poured into a concentric mold in order to cast a tube, with or without a fabric matrix within the mold. The crosslinking reaction is allowed to proceed at room temperature (22° C.) and 58 percent relative humidity for at least 24 hours and to reduce the moisture content. The semi-solid hydrogel is slipped out of its concentric mold to form a tubular structure suitable for use as an artery-like prosthesis. The tubes were then subjected to a vapor phase crosslinking reaction and after-treatments as described in Example 5.

EXAMPLE 7

BONE-LIKE PROSTHESES

The starting raw material for producing both cancellous-like and cortical-like prostheses from the stabilized natural protein polymer hydrogels of this invention may be as described in Example 5. One of the major differences involves the use of phosphoric acid in preference to hydrochloric acid to adjust the acidity of the hydrogel prior to the addition of the crosslinking reagent.

The initial water-soluble non-crystalline natural protein solution has intimately dispersed within it calcium phosphate particles or crystals with or without inclusion of other ions such as are found in naturally occurring bone and cartilage. The product consists primarily of an intimate and homogenous physical mixture of the various ingredients and various ions may be included to increase the hardness of the product prior to the addition of the protein crosslinking agents described in prior examples.

The calcium phosphate may be formed by mixing solutions of a soluble calcium salt, such as calcium acetate, and of a soluble phosphate, such as sodium phosphate. In the event other salts and/or ions are to be included, such as the fluoride or carbonate ions, soluble salts, such as calcium fluoride or sodium carbonate, may be incorporated in the salt solutions during the formation of the calcium phosphate. The precise structure of the calcium phosphate compounds formed are complex and the term "calcium phosphate" is used to include dicalcium phosphate, tricalcium phosphate, octacalcium phosphate, hydroxyapatite, carbonateapatite, chlorapatite, fluorapatite, and mixtures thereof.

A modification of Example 5 found to be desirable in producing extremely porous, cancellous-type prostheses is the replacement of water as the protein solvent with a dilute aqueous solution of hydrogen peroxide, for example, a 1 percent by volume aqueous solution. Following dissolution of the protein in the dilute solution of hydrogen peroxide, a sufficient amount of a 25 percent (by weight) aqueous slurry of calcium phosphate was incorporated into the protein solution to provide approximately equal amounts of protein and calcium phosphate. The pH was then adjusted with phosphoric acid and the crosslinking agent (ammonium alum) added and the mixture vigorously agitated while maintaining the temperature at 60°±5° C. The use of the hydrogen peroxide solution as the protein solvent results in the formation of small uniformly dispersed bubbles during the adjustment of the pH and addition of the crosslinking agent and thus forms a uniformly porous structure during crosslinking.

The mixture is cast or shaped into the desired structural configuration. It is then transferred to a suitable chamber wherein it is subjected to a vapor phase crosslinking reaction and after-treatment as described in Example 5. Because of the usual relatively bulky size of bone-like structures, the vapor phase crosslinking reaction is preferably prolonged to 150 hours or even longer as compared to the shorter periods for films.

EXAMPLE 8

FIBERS, TEXTILE PRODUCTS, AND SUTURES

The same composition of water soluble protein hydrogel described for Example 1 is a suitable starting raw material for producing novel fibers capable of being fashioned into many conventional textile forms—webs, fabrics, mats, etc.

The deaerated acidified gel (pH 4.5) is pumped into an antichamber in sequence with a mechanism capable of extruding the hydrogel through spinnerets to form ultrafine fibers or even monofils; such equipment is commonly used in producing viscose rayon and cellulose acetate filaments.

The temperature of the gel is kept at 60°±5° C. in the antichamber, prior to being passed through a mixing pump. The filaments are continuously extruded into long vertical cylindrical chambers in which the temperature is reduced to about room temperature and are partially dried. The filaments are then collected on reels or in the form of skeins. The reels and skeins are placed in a suitable chamber and subjected to vapor phase crosslinking reaction and aftertreatment as described in Example 5.

Such fibers are suitable for a variety of medical and apparel uses. When extruded in the form of small diameter filaments, they may be used as sutures for surgery.

The foregoing examples are representative of the method of this invention and are not to be considered as limitations. For example, in the examples, formaldehyde has been used as the covalent crosslinking agent because of its relatively low cost and ready availability; equivalent amounts of any other covalent agent may be substituted for the formaldedhyde. It is apparent that modifications and variations in the constituents and proportions may be made without departing from the spirit and scope of the invention.

What is claimed is:

1. The method of preparing a three-dimensional structure comprising preparing an aqueous acidic solution of a non-crystalline, natural animal or vegetable protein polymer or mixtures thereof, the polymers having an average molecular weight not exceeding 100,000, shaping the solution into a three-dimensional structure, subjecting the structure to a vapor phase crosslinking reaction using at least two crosslinking agents in vaporized state to form a crosslinked polymer structure, subjecting the structure to washing with water, subjecting the washed structure to dehydration by immersion in water-miscible organic solvent mixture, subjecting the structure to washing with water and drying the structure to a moisture content of not more than 10 percent.

2. The method as defined in claim 1 wherein the solution of the protein contains at least one crosslinking agent.

3. The method as defined in claim 1 wherein following the vapor phase crosslinking reaction the structure is immersed in a water-organic solvent mixture containing at least 1 crosslinking agent.

4. The method as defined in claim 1 wherein during the vapor phase crosslinking reaction the structure is subjected to UV and/or gamma radiation.

5. The method as defined in claim 1 wherein following the vapor phase crosslinking reaction the structure is immersed in a water-organic solvent mixture containing at least 1 crosslinking agent and during both crosslinking reactions the structure is subjected to UV and/or gamma radiation.

6. The method as defined in claim 1 wherein the aqueous acidic solution of the protein polymer has a pH of from about 3.5 to about 5.5.

7. The method as defined in claim 1 wherein the protein polymer is an animal protein.

8. The method as defined in claim 1 wherein the protein polymer is gelatin.

9. The method as defined in claim 1 wherein the protein polymer is a vegetable protein.

10. The method as defined in claim 1 wherein the aqueous acidic solution of the protein polymer is an aqueous hydrochloric acid solution of animal protein and has a pH of from about 3.5 to about 5.5.

11. The method as defined in claim 1 wherein the aqueous acidic solution of the protein polymer is an aqueous hydrochloric acid solution of gelatin having a pH of from about 3.5 to about 5.5.

12. The method as defined in claim 1 wherein the aqueous acidic solution of the protein polymer is an aqueous hydrochloric acid solution of gelatin having a pH of from about 3.5 to about 5.5 and the vapor phase crosslinking agents are formaldehyde and glutaraldehyde in vaporized state.

13. The method as defined in claim 1 wherein the water-miscible organic solvent is ethanol.

14. The method as defined in claim 1 wherein the aqueous acidic solution of the protein polymer is an aqueous hydrochloric acid solution of gelatin having a pH of 3.5 to 5.5, the vapor phase crosslinking agents are formaldehyde and glutaraldehyde in vaporized state, following the vapor phase crosslinking reaction the structure is immersed in a water-organic solvent mixture containing formaldehyde and glutaraldehyde.

15. The method as defined in claim 1 wherein the aqueous acidic solution of the protein polymer is a solution of an animal protein having a pH of from about 3.5 to about 5.5, a slurry of calcium phosphate is incorporated in the acidic solution and the protein polymer-calcium phosphate mixture is shaped into a three-dimensional structure.

16. A unitary three-dimensional structure having unique wet-strength properties comprising a cross-linked, non-crystalline natural animal or vegetable protein polymer or mixtures thereof, the polymers having an average molecular weight not exceeding 100,000 and formed by the method as defined in claim 1.

17. A unitary three-dimensional structure as defined in claim 16 which include calcium phosphate.

18. A unitary three-dimensional structure as defined in claim 16 in the form of a soft contact lens.

19. A unitary three-dimensional structure as defined in claim 16 in the form of a film.

20. A unitary three-dimensional structure as defined in claim 16 in the form of a filament.

* * * * *